United States Patent [19]

Watt-Smith

[11] Patent Number: 4,659,714

[45] Date of Patent: Apr. 21, 1987

[54] ANESTHETIC METHODS FOR MAMMALS

[75] Inventor: Stephen R. Watt-Smith, London, England

[73] Assignee: Dentsply, Ltd., Weybridge, England

[21] Appl. No.: 593,724

[22] Filed: Mar. 27, 1984

[51] Int. Cl.⁴ .................. A61K 31/505; A61K 31/44; A61K 31/445; A61K 31/415; A61K 31/24; A61K 31/165; A61K 31/135

[52] U.S. Cl. .................................. 514/260; 514/280; 514/317; 514/385; 514/401; 514/535; 514/617; 514/615; 514/646; 514/816; 514/817; 514/818

[58] Field of Search ................. 514/40, 280, 317, 816, 514/817, 818, 401, 385, 535, 617, 646, 615

[56] References Cited

U.S. PATENT DOCUMENTS 3,605,744 9/1971 Dwyer .................................. 604/51

OTHER PUBLICATIONS

Modern Drug Encyclopedia, 16th ed., 1981, p. 772.
Unlisted Drugs, vol. 24(4): 57(1), 1972.
Merck Index, 9th ed, 1976, Nos. 9267, 9769, 9771 and 7509.

Primary Examiner—Donald B. Moyer
Assistant Examiner—John W. Rollins
Attorney, Agent, or Firm—Woodcock Washburn Kurtz Mackiewicz & Norris

[57] ABSTRACT

Improved methods of anesthesia for mammals, especially humans, are provided wherein the prolonging effect upon local anesthesia which is exhibited by co-administration of vasoconstrictors, especially vasoconstrictors believed to act upon alpha adrenoreceptor sites on blood vessel walls, are provided. In accordance with a preferred embodiment, alpha adrenoreceptor blocking agents are aministered subsequent to the performance of surgery or dentistry under local anesthesia accomplished through co-administration of anesthesia and vasoconstrictor to cause reduction of prolonged anesthetic effect. Seriatim procedures are facilitated under local anesthesia through employment of the present invention. Improved patient aesthetics, diminution of self-inflicted trauma, and increased sensory feedback from patients are among the benefits conferred by the present invention.

9 Claims, 1 Drawing Figure

ANESTHETIC METHODS FOR MAMMALS

BACKGROUND OF THE INVENTION

The present invention is directed to improved methods for anesthesia in mammals, especially humans. More particularly, improved procedures for local anesthesia are provided which overcome many of the shortcomings of prior methods. The present invention is directed to procedures for anesthesia, especially "local" anesthesia of the regions in and around the mouth. In the present context, "local" anesthesia includes all forms of soft tissue anesthesia including infiltrative and "blocking" anesthesia. As applied to anesthesia of the mouth and associated regions, the present invention is directed to all forms of such anesthesia, especially infiltrative soft tissue anesthesia, alveolar, mandibular, and other blocks and those other means of local anesthesia appropriate to oral surgery, dental restoration, and the like which are known to those of ordinary skill of the art.

As traditionally practiced, oral anesthesia comprises the application, such as by injection, of one or more anesthetic agents into appropriate regions of the mouth and surrounding tissues. In common practice, vasoconstrictors such as catchecolamines including epinephrine, norepinephrine and similar species together with other vasoconstrictors, may be added to anesthetics to prolong the duration of anesthesia in the highly vascular environment of the mouth. This prolongation of the anesthetic effect is beneficial from the standpoint of providing increased working time for the oral surgeon or dentist, but suffers from certain shortcomings. Thus, self-inflicted tongue, lip, and cheek ulcerations are commonly seen as a result of the prolonged loss of soft tissue sensation in the mouth. Such physical injury may be more harmful than the oral procedure itself. Corollarily, the persistence of anesthesia in oral tissues interferes with the normal activities of patients receiving oral anesthesia coupled with vasoconstriction co-treatment; patient dissatisfaction may result. The employment of vasoconstrictors with oral anesthetics leads to further difficulties from a practical standpoint. Thus, it is difficult to secure patient information requiring oral sensation when vasoconstrictors are co-administered with oral anesthetics. It is, accordingly, necessary to detain a patient for a significant period of time if such information, such as the feel or comfort of an oral restoration, is to be obtained. Patient "feedback" is therefore difficult to obtain. Moreover, it is inconvenient to work on more than one section of a mouth during one visit to an oral surgeon or dentist since simultaneous local anesthesia of pluralities of mouth regions is generally contraindicated.

SUMMARY OF THE INVENTION

It has now been discovered that the effect of the co-application of anesthetics and vasoconstrictors may be substantially reduced or reversed through administration of an alpha adrenoreceptor blocking agent to the anesthetized area. The prolongation of the anesthetic effect of anesthetic obtained through the co-application of a vasoconstrictor with the anesthetic may be terminated or reduced through application of such alpha adrenoreceptor blocking agents to anesthetized body portions of mammals. In accordance with a preferred method, the vasoconstrictor has a mode of action similar to that believed to be employed by catchecolamine vasoconstrictors.

Accordingly, the present invention is directed to methods of treating a mammal comprising applying an anesthetic agent to a portion of the body of the mammal and co-applying to the body portion an amount of a vasoconstrictor sufficient to prolong the anesthetic effect of the anesthetic agent such as by causing constriction of blood vessels in said portion. Subsequent to the application and co-application, an alpha adrenoreceptor blocking agent is administered to said body portion in an amount sufficient substantially to reduce or reverse the prolongation.

In accordance with a preferred embodiment of the present invention, the application of anesthetic agent and co-application of vasoconstrictor takes place substantially simultaneously, such as through injection of a single solution containing both such agents.

In accordance with another preferred embodiment, the administration of blocking agent is preceded by the performance of one or more oral surgical or dental procedures in or adjacent to the body portion.

OBJECTS OF THE INVENTION

It is a principal object of this invention to provide methods for treating mammals, especially humans, to effect anesthesia thereof, especially local anesthesia.

Another object is to provide means for reversing the prolongation of local anesthesia caused by co-administration of a vasoconstrictor with an anesthetic.

Yet another object is to permit the seriatim treatment of several body portions of an individual mammal under anesthetic conditions.

A further object is to provide methods for performing oral surgical or dental procedures under anesthesia wherein patient "feedback" requiring the employment of oral sensation may be obtained rapidly and predictably.

A further object is to provide compositions of matter useful in the reversal of prolongation of anesthetic effect in local anesthesia comprising an alpha adrenoreceptor blocking agent in a pharmaceutically acceptable carrier, the blocking agent being present in an amount sufficient to cause reversal of the prolonging effect.

Yet another object is to provide improved means for the employment of catchecolamine-derived vasoconstrictor agents in local anesthesia whereby the prolonging effect of such catchecolamine-derived materials may be reduced or reversed at will.

Still further objects will become apparent from a review of the present specification.

DETAILED DESCRIPTION OF THE INVENTION

Figure 1:
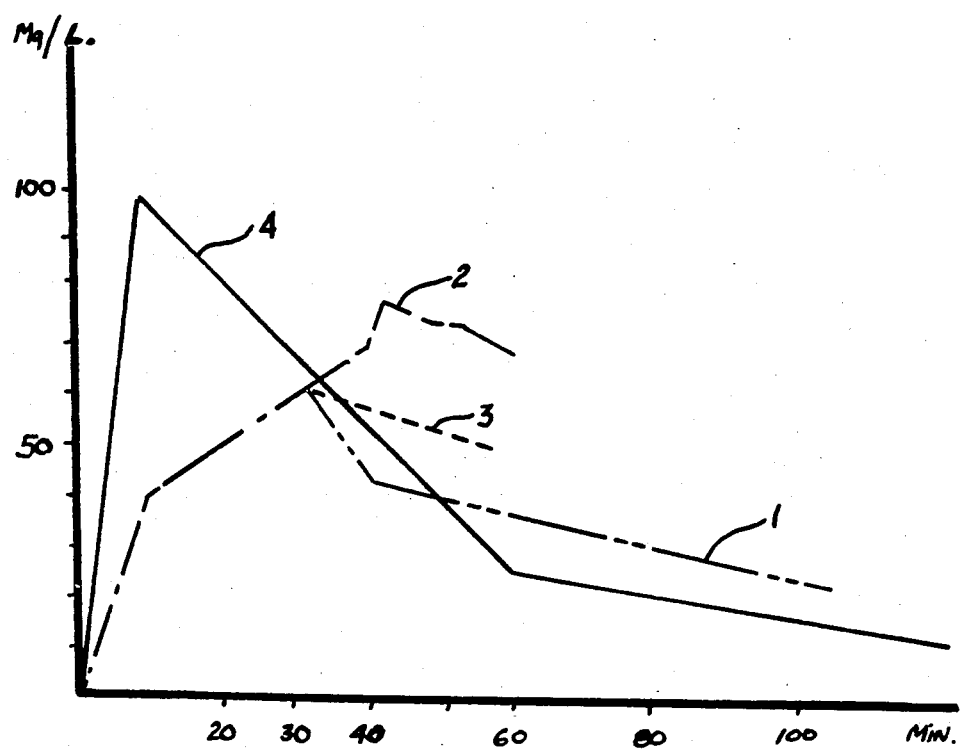
FIG. 1 depicts the blood concentration of lignocaine in human subjects in milligrams per liter as a function of time after injection of 6 milliliters of 2% lignocaine admixed with epinephrine before and after subsequent administration of phentolamine or a placebo.

The employment of vasoconstrictors in conjunction with anesthetics has been well-received, especially by the dental profession. The shortcomings of self-inflicted trauma, patient dissatisfaction, and difficulty in obtaining patient sensory "feedback" have been recognized, however. While these shortcomings have not yet led to abandonment of the use of vasoconstrictors in conjunction with local anesthetics, some procedure for minimizing those shortcomings in the approximately 70% of patients who receive vasoconstrictors in conjunction with anesthetics has long been desired.

While the mechanism of action of vasoconstrictors, including the catchecolamines, has not yet been fully elucidated, it is believed that they may operate upon alpha adrenoreceptor sites thought to be present in the walls of blood vessels, to cause constriction of the vessels. The vasoconstrictive effect of these materials is believed to result in the isolation of the anesthetic material in the location where it is placed for an increased period of time thereby prolonging the time wherein the anesthetic effect is experienced.

It has now been found that application or administration of a composition which is believed to act as an alpha adrenoreceptor blocking agent may serve to counteract the vasoconstrictive effect of vasoconstrictors, especially those vasoconstrictors which are believed to act upon the alpha adrenoreceptors of mammalian blood vessel walls. While it is not desired to be bound by any particular theory in explaining the demonstrated phenomena of the present invention, it is believed that competitive inhibition of the effect of the foregoing vasoconstrictors by the alpha adrenoreceptor blocking agents leads to this reversal.

Even if vasoconstrictors do not operate upon alpha adrenoreceptor sites on the walls of blood vessels or even if vasoconstrictors different from the catchecolamines and other materials which are believed to operate upon such sites are employed, the employment of alpha adrenoreceptor blocking agents may nonetheless serve to tend to retard or reverse the prolonging effect of such compositions upon local anesthesia. Thus, the known effect of alpha adrenoreceptor blocking agents to cause vasodilation is believed to result in increased blood flow through the body portion treated with anesthetic, thus to flush the anesthetic from the region in a relatively short period of time, causing relatively rapid termination of the anesthetic effect.

While the ability of alpha adrenoreceptor blocking agents to cause vasodilation has been known, and while the competitive inhibitory effects of such blocking agents upon the mechanism of action of certain vasoconstrictors which act upon alpha adrenoreceptor sites has been suggested, it has never been proposed to limit or reverse the prolongation of anesthetic effect caused by employment of vasoconstrictors concomitantly with anesthetics through the use of such alpha adrenoreceptor blocking agents.

The anesthetics useful in the practice of the present invention may be any of those anesthetics which are known for anesthesia, especially for "local" anesthesia. Such anesthetics include any of those useful for infiltrative anesthesia, blocking anesthesia, or for any other form of anesthesia known to those skilled in the art. Among the foregoing are included lignocaine, procaine, prilocaine, amethocaine, bupivacaine, cinchocaine, mepivacaine and many others. It is believed that the mechanism of action of the alpha adrenoreceptor blocking agents of the present invention is largely independent of the identity of the anesthetic agent employed. The object of the blocking agent is to release the anesthetic from the proximity of the body portion to which it has been applied in order to reverse its effects.

The vasoconstrictive agents which are useful in the practice of the present invention may be any of the compositions known to those skilled in the art to be effective in causing constriction of blood vessels in a localized area of the body of a mammal, especially a human. Preferred among the foregoing are classes of compositions which are believed to act upon alpha adrenoreceptor sites on the wall of such blood vessels. These materials include the catchecolamines and catchecolamine derivatives exemplified by epinephrine, norepinephrine, adrenaline and numerous other species known or believed by those skilled in the art to have alpha adrenoreceptor vasoconstructive effect. It may also be possible to include vasoconstrictive materials other than those which act upon alpha adrenoreceptors. In this regard, the effects of the alpha adrenoreceptor blocking agents in reversing the prolongation of anesthetic effect by such vasoconstrictors would likely take place through a mechanism different from the competitive inhibition mechanism proposed above. In any event, it is believed that the present invention may be applicable to a wide variety of vasoconstrictors to greater or lesser degree.

Alpha adrenoreceptor blocking agents useful in the practice of the present invention may be any of that class of materials which is believed competitively to interfere with alpha adrenoreceptive sites on the walls of blood vessels in mammals, especially humans, to militate the effect of vasoconstrictors, especially catchecolamines, thereupon. Such material includes phentolamine, phentolamine mesylate, phentolamine hydrochloride, yohimbine, rauwolscine, doxazosin, labetalol, prazosin, tolazoline and other materials known to those skilled in the art to have the foregoing effects.

The methods in accordance with the present invention are generally directed to the treatment of mammals, especially humans. Generally, an anesthetic agent is applied to a portion of the body of the mammal to be treated. This application may be via any of those methods presently known to those skilled in the art, such as via injection. The application is preferably generally of the type known to result in local anesthesia. Thus, the anesthetic agent may be infiltrated into soft tissue, or may be applied at a selected site to invoke a "block". In connection with oral and dental procedures, mandibular or alveolar nerve blocks are commonly employed. Other means for effecting local anesthesia may also be employed, however.

The present methods further comprise the co-application to the portion to be anesthetized of an amount of a vasoconstrictor sufficient to prolong the effect of the anesthetic agent in the treated body portion. It is preferred that the vasoconstrictor be one of those compositions which are believed to interact with alpha adrenoreceptor sites which ae believed to be present in walls of blood vessels. Other vasoconstrictors may also be useful, however, as noted above. It is believed that an effect of the vasoconstrictor is to partially isolate the treated body portion from normal blood flow thus to cause increased residence time of the anesthetic agent in that locality. Prolongation of the anesthetic effect results thereby.

The application of anesthetic agent and co-application of vasoconstrictor are preferably and conveniently accomplished simultaneously. In this regard, they may conveniently be mixed into a unitary, injectable solution, preferably in a pharmaceutically acceptable carrier, for injection into the mammalian site to be anesthetized.

Subsequent to the application of anesthetic agent and co-application of vasoconstrictor, an alpha adrenoreceptor blocking agent is administered to cause substantial reduction or reversal of the prolongation of anesthetic effect in the area of the body to be treated. The blocking agent is employed in amounts sufficient substantially to reverse, retard or reduce the prolongation of anesthesia effected by the vasoconstrictor. The administration of the blocking agent is not undertaken until such time as reversal is desired. As presently envisioned, the period of time between application and co-application of anesthetic agent and vasoconstrictor and the administration of blocking agent to cause reversal of the prolonged anesthetic effect is preferably employed for the performance of surgery, dental restoration, or other procedures. Accordinly, the surgeon or dentist may avail himself of the prolonged effect of anesthesia which is the result of the employment of the vasoconstrictor but may cause the same to be reversed, at will, upon the application of the blocking agent.

The alpha adrenoreceptor blocking agent is preferably applied to the mammalian body portion in accordance with the invention either alone or in admixture with a pharmaceutically acceptable carrier. The blocking agent may be applied to such body portion via any convenient means which is effective to result in substantial reversal of the prolonged anesthetic effect. Injection of the blocking agent may be found to be convenient and effective as may other forms of application such as topical application of a fluid, paste, gel, tablet or the like containing the agent. Application of the agent should be in an amount sufficient substantially to reverse or retard the prolonged anesthetic effect.

In accordance with the foregoing procedure, it is possible to reverse the numbness and other anesthetic effects which are experienced by a patient after anesthesia prolonged through the use of vasoconstrictors. Accordingly, the patient is far less liable to self-inflicted injury than is a patient whose prolonged anesthesia is not reversed. Moreover, the return of sensation to the patient enables him to report to the physician or dentist on the sensory perception of the previously anesthetized body portion. In such a fashion the dentist or surgeon may be able to ascertain more accurately the effects of the treatment performed. Proper occlusion of dental structures after restoration, the proper fit of dental appliances and many other properties incident to dental restorative work may thus be ascertained.

Since the effect of the anesthetic may now be limited to a preselected time, additional body portions, subsequent to an initial treatment, may also be locally anesthetized in accordance with the present invention. Thus, a maximum amount of oral surgery or dentistry may be accomplished in one consultation, leading to greater efficiencies in practice and to greater convenience to patients.

In accordance with the present invention, there is also provided a composition suitable for reducing or reversing the prolonging effects of anesthesia caused by vasoconstrictors. Thus, it is presently contemplated that compositions comprising an alpha adrenoreceptor blocking agent in a pharmaceutically acceptable carrier will be provided, the blocking agent being present in an amount sufficient to retard or reverse the prolonging effects of anesthesia caused by the vasoconstrictor. One preferred composition comprises an alpha adrenoreceptor blocking agents in a pharmaceutically acceptable carrier having properties adapted to administration by injection adjacent to the site the anaesthesia of which is to be reduced or curtailed.

The following examples are intended as exemplary only and are not to be construed as limiting.

EXAMPLE 1

Patients were injected orally with standard dosages of 1 ml of lignocaine admixed with epinephrine (0.0125 mg/ml) through infiltration. After 30 minutes, injection of 0.5 ml of either a placebo or phentolamine alpha adrenoreceptor blocking agent in the indicated concentrations in a pharmaceutically acceptable carrier was performed. The numbers of subjects, duration of anesthesia following second injection, and concentrations of phentolamine are given in the following table:

TABLE I

| Group | Concentration of Phentolamine (mg/ml) | Duration of Anesthesia (min) | n |
|---|---|---|---|
| 1 | 0 | 137 | 10 |
| 2 | 1 | 24 | 20 |
| 3 | 1.4 | 22 | 20 |
| 4 | 2.0 | 17 | 40 |
| 5 | 3.0 | 15 | 10 |

At a concentration of 2.0 mg/ml, duration of anesthesia after the second injection was about 17 minutes compared with 137 minutes for the placebo. An rho value of less than 0.001 was calculated indicating highly significant statistical results.

EXAMPLE 2

The effects of alpha adrenoreceptor blocking agents upon the anesthetic prolongation effected by epinepherine in inferior alveolar nerve blocks were studied. Aveolar nerve blocks were accomplished through injection of subjects with 2 ml of lignocaine with epinephrine (0.0125 mg/ml) followed after 30 minutes by similar injection of 1 ml of phentolamine at a concentration of 2 mg/ml or of a placebo. Duration of anesthesia following the second injection for the placebo was approximately 160 minutes for 10 subjects. The duration of anesthesia for the 10 treated subjects was approximately 17 minutes. A calculated rho value of less than 0.001 was again found indicating highly significant effects.

EXAMPLE 3

To ascertain whether multiple reversals of anesthesia prolongation could be accomplished in the same individual, a group of 5 subjects was injected peri-orally both through infiltration and through inferior alveolar nerve blocks with 6 ml of 2% lignocaine containing epinephrine (0.0125 mg/ml). After a latency of 30 minutes, four 0.5 ml increments of phentolamine reversing agent at a concentration of 2 mg in 1 ml of carrier, or a placebo was injected in a similar manner. Blood samples were taken of the subjects over time to determine the levels of lignocaine present therein. The cardiovascular system was analyzed during the term of the experiment to determine whether any adverse reaction to the lignocaine or phentolamine was exhibited. The results are summarized in FIG. 1. Curve 1 represents the lignocaine level over time without a second injection while curves 2 and 3 depict the levels after injection of the phentolamine or placebo respectively. The effects of lignocaine injection without epinephrine were also plotted as curve 4. The figure demonstrates the antagonistic effect of phentolamine on the vasoconstrictor indicated by the temporary rise in blood lignocaine concentration following its administration. This supports the hypothesis that alpha adrenoreceptor blocking agents are effective at reducing residual soft tissue anesthesia produced by local anesthetics containing vasoconstrictors such as epinephrine, presumably through competitive inhibition of the alpha adrenoreceptor sites. The levels of lignocaine achieved by the recommended procedure were consistantly less than the known therapeutic levels used for the treatment of cardiac arrhythmias indicating the practicality of multiple reversals.

EXAMPLE 4

Phentolamine was injected to reverse residual soft tissue anesthesia produced by vasoconstrictors which are believed not to coact with alpha adrenoreceptors on the walls of blood vessels in mammals. There was no significant reversal of soft tissue anesthesia produced by 6 ml of 3% prilocaine plus 0.03 of felypressin, a non-catchecolamine vasoconstrictor when phentolamine reversing agent was injected as four 0.5 ml increments of 2 mg/ml solution. Blood assays for prilocaine confirmed no significant uptake from the soft tissues after the attempt at reversal using phentolamine. There were no demonstrable cardiovascular changes during the trial. Although phentolamine does not reverse the soft tissue residual anesthesia produced by this combination of anesthetic and vasoconstrictor under the given circumstances, the experiment demonstrates that when a non-catchecolamine-containing local anesthetic is injected and reversal with phentolamine attempted, no significant cardiovascular changes are discernable.

What is claimed is:

1. The method of anesthetizing the mouth of a mammal comprising the steps of:
applying an anesthetic agent to at least a portion of the mouth of the mammal; the improvement comprising co-applying to said mouth portion an amount of a vasoconstrictor sufficient to prolong the anesthetic effect of the anesthetic agent upon the mouth portion; and subsequent to said applications administering an alpha adrenoreceptor blocking agent to said mouth portion in an amount sufficient to reduce the prolongation.

2. The method of claim 1 wherein said co-application is simultaneous with said application.

3. The method of claim 1 wherein each of said applying, co-applying and administering steps is accomplished through injection.

4. The method of claim 3 wherein said anesthetic effect is accomplished through infiltration or blocking.

5. The method of claim 1 wherein the anesthetic agent comprises a local or topical anesthetic.

6. The method of claim 1 wherein the anesthetic agent is selected from the group consisting of lignocaine, xylocaine, novacaine, carbocaine, procaine, prilocaine, bupivacaine, cinchocaine and mepivacaine.

7. The method of claim 1 wherein the vasoconstrictor comprises a catchecolamine or catchecolamine derivative.

8. The method of claim 1 wherein the vasoconstrictor is selected from the group consisting of epinephrine and norepinephrine.

9. The method of claim 1 wherein the blocking agent is selected from the group consisting of phentolamine, phentolamine hydrochloride, phentolamine mesylate, tolazoline, yohimbine, rauwolscine, doxazosin, labetolol and prazosin.

* * * * *